(12) United States Patent
New et al.

(10) Patent No.: US 6,471,979 B2
(45) Date of Patent: Oct. 29, 2002

(54) APPARATUS AND METHOD FOR DELIVERING COMPOUNDS TO A LIVING ORGANISM

(75) Inventors: Gishel New, New York, NY (US); Jeffrey W. Moses, New York, NY (US); Nicholas Kipshidze, New York, NY (US); Gary S. Roubin, New York, NY (US); Martin B. Leon, New York, NY (US)

(73) Assignee: Estrogen Vascular Technology, LLC, New York, NY (US)

( * ) Notice: Subject to any disclaimer, the term of this patent is extended or adjusted under 35 U.S.C. 154(b) by 0 days.

(21) Appl. No.: 09/943,648

(22) Filed: Aug. 30, 2001

(65) Prior Publication Data
US 2002/0072511 A1 Jun. 13, 2002

Related U.S. Application Data

(63) Continuation-in-part of application No. PCT/US00/35641, filed on Dec. 29, 2000.
(60) Provisional application No. 60/173,451, filed on Dec. 29, 1999.

(51) Int. Cl.[7] .................... A61K 31/565; A61M 25/10; A61M 29/00; A61P 9/10; A61F 2/01
(52) U.S. Cl. .................... 424/422; 424/423; 514/182; 514/824; 623/1.42; 623/1.43; 604/264; 604/93; 604/915
(58) Field of Search ................. 424/422, 423; 514/182, 824; 623/1.42, 1.43; 604/264, 93, 915

(56) References Cited

U.S. PATENT DOCUMENTS

| | | |
|---|---|---|
| 5,242,397 A | 9/1993 | Barath et al. |
| 5,695,514 A | 12/1997 | Chin |
| 5,782,741 A | 7/1998 | Bradshaw et al. |
| 5,797,878 A | 8/1998 | Bleam |
| 5,865,748 A | 2/1999 | Co et al. |
| 5,866,561 A | 2/1999 | Ungs |
| 5,868,763 A | 2/1999 | Spence et al. |
| 5,911,685 A | 6/1999 | Siess et al. |
| 5,921,913 A | 7/1999 | Siess |
| 5,921,979 A | 7/1999 | Kovac et al. |
| 5,957,835 A | 9/1999 | Anderson et al. |
| 5,962,475 A | 10/1999 | Schmid et al. |
| 5,964,694 A | 10/1999 | Siess et al. |
| 5,976,069 A | 11/1999 | Navia et al. |
| 5,980,503 A | 11/1999 | Chin |
| 6,019,722 A | 2/2000 | Spence et al. |
| 6,048,300 A | 4/2000 | Thornton et al. |
| 6,083,257 A | 7/2000 | Taylor et al. |
| 6,113,613 A | 9/2000 | Spaulding |
| 6,153,252 A | 11/2000 | Hossainy |
| 6,206,827 B1 | 3/2001 | Chin et al. |
| 2001/0037144 A1 | 11/2001 | Kim et al. |

FOREIGN PATENT DOCUMENTS

| | | |
|---|---|---|
| CA | 2282982 | 3/2001 |
| CA | 2300246 | 9/2001 |
| WO | WO01/00109 A1 | 1/2001 |

*Primary Examiner*—Edward J. Webman
*Assistant Examiner*—Helen Nguyen
(74) *Attorney, Agent, or Firm*—Michael Best & Friedrich LLP

(57) ABSTRACT

A method of treating or preventing vascular disease in a living organism. The method includes delivering an effective amount of a composition including a sex hormone, antihormone, sex-hormone agonist, steroid-hormone inhibitor/antagonist (partial or full), selective estrogen receptor modulator (SERM), or a combination thereof, to an affected area of a living organism.

7 Claims, 5 Drawing Sheets

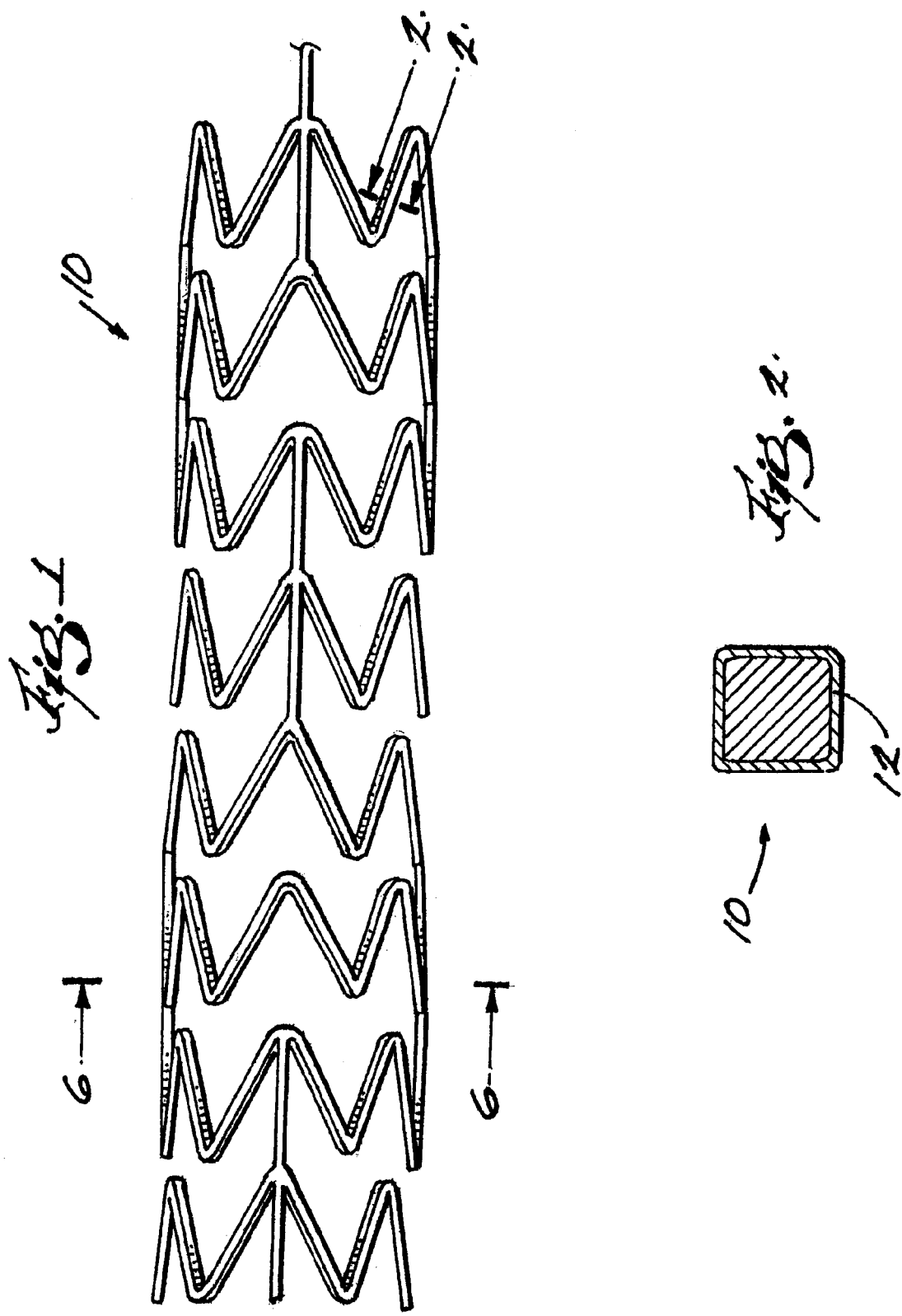

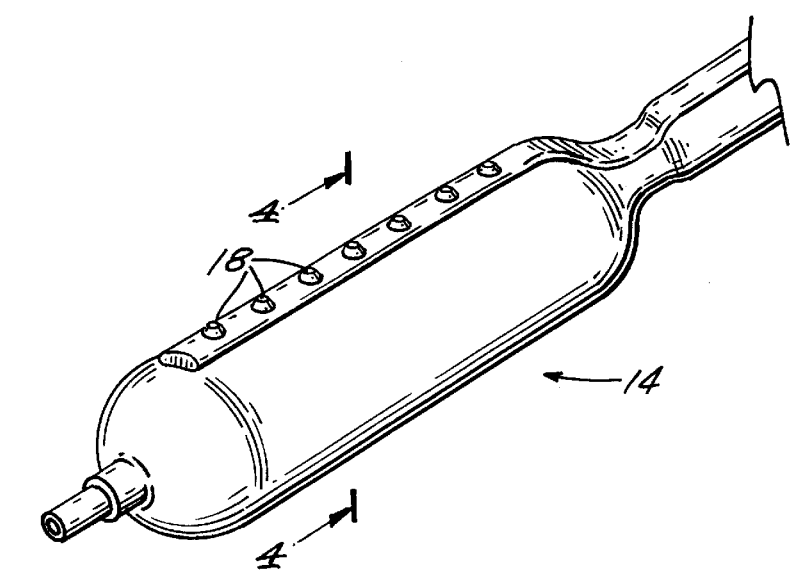
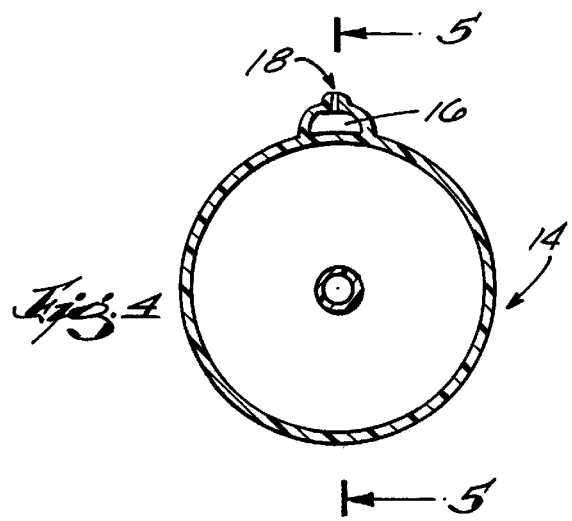
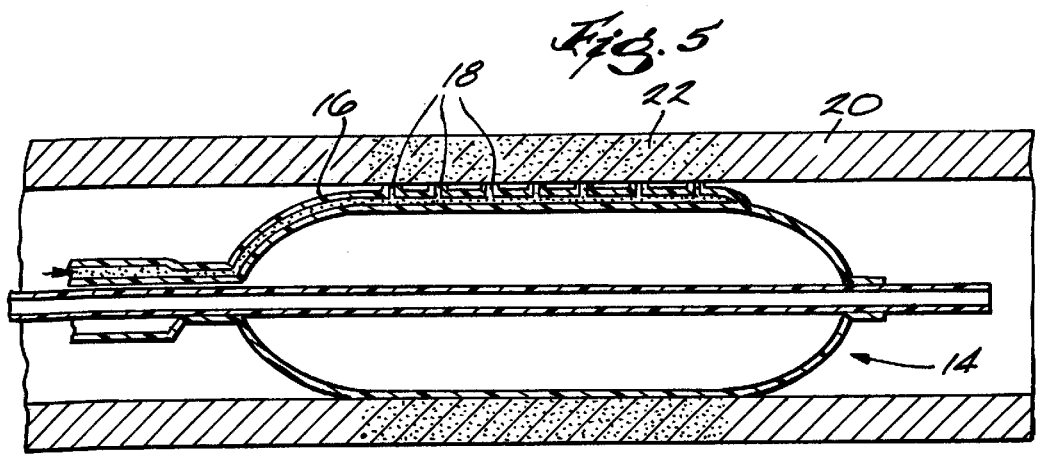

|  | Control | Low Dose | High Dose | P value |
|---|---|---|---|---|
| Vessel Area | 9.69 ±2.21 | 9.92±2.04 | 10.45±1.45 | NS |
| Luminal Area | 3.49 ± 1.41 | 4.20 ± 1.74 | 5.4 ± 1.70 | NS |
| Intimal Area (IA) | 4.13 ± 1.1 | 3.60±0.79 | 2.54± 1.0 | <0.05 |
| Stent Strut Area (SSA) | 7.61 ± 1.70 | 7.80±1.53 | 8.01 ± 1.23 | NS |
| Injury Score | 21±0.47 | 2.19±0.43 | 2.0±0.61 | NS |
| IA/Injury Score | 1.96 ± 0.32 | 1.66 ± 0.33 | 1.32 ± 0.40 | <0.01* |
| Eudothelialization Score | 3+ | 3+ | 3+ | NS |

All values are mean ± SD.

P-value for control vs high dose (ANOVA post-test with Bonferroni correction)

Figure 7

| Study | Stent & balloon description | Average Dosage (µg per stent) | Range (µg per stent) | Average Dosage per area (µg/mm²) | Range (µg/mm²) |
|---|---|---|---|---|---|
| "High Dose" Loading Protocol used in Preclinical trial | 18mm OC stent premounted on 4mm diameter balloon. | 240 (n=3) | 229-254 | 3.0 | 2.8-3.2 |
| Verification Study | 18mm OC premounted on 3mm diameter balloon. | 259 (n=5) | 243-276 | 2.6 | 2.4-2.8 |

Figure 8

| Average Dosage (µg per stent) | Standard Dev Dosage (µg per stent) | Average dosage (µg/mm²) | Standard Dev (µg/mm²) |
|---|---|---|---|
| 252 | 15 | 2.54 | 0.15 |

Figure 9

| Stent design | Surface Area (mm²) | Average dosage (µg per stent) | Std dev (µg per stent) |
|---|---|---|---|
| 11OC | 61.56 | 156 | 9 |
| 15OC | 80.40 | 204 | 12 |
| 18OC | 99.24 | 252 | 15 |

Figure 10

APPARATUS AND METHOD FOR DELIVERING COMPOUNDS TO A LIVING ORGANISM

CROSS-REFERENCE TO RELATED APPLICATIONS

This application is a continuation-in-part (CIP) of international application no. PCT/US00/35641 filed on Dec. 29, 2000 which claims priority to U.S. application patent Ser. No. 60/173,451 filed on Dec. 29, 1999.

FIELD OF THE INVENTION

The invention relates to local-delivery devices and methods for treating and preventing proliferative and atherosclerotic vascular diseases in a living organism. More particularly, the invention relates to local-delivery devices coated with a composition comprising a sex hormone, anti-hormone, sex-hormone agonist, steroid-hormone inhibitor/antagonist (partial or full), selective estrogen receptor modulator (SERM), or a combination thereof. The local-delivery device, e.g. a stent, catheter or balloon-injection catheter in situ to coat the implanted stent, is inserted into an affected area of a living organism to treat or prevent the proliferative and atherosclerotic vascular disease.

BACKGROUND OF THE INVENTION

Vascular diseases include diseases that affect areas of a living organism relating to or containing blood vessels. For example, stenosis is a narrowing or constricting of arterial lumen in a living organism (e.g., a human) usually due to atherosclerosis/coronary heart disease (CHD). Restenosis is a recurrence of stenosis after a percuteneous intervention such as angioplasty and stenting. Restenosis typically affects the large arteries of a living organism. The underlying mechanisms of restenosis comprise a combination of effects from vessel recoil, negative vascular remodeling, thrombus formation and neointimal hyperplasia. It has been shown that restenosis after balloon angioplasty is mainly due to vessel remodeling and neointimal hyperplasia and after stenting is mainly due to neo-intimal hyperplasia.

Treatment for stenosis and restenosis varies. Stenosis caused by CHD often forces individuals to restrict and limit their activity levels in order to avoid complications, stroke, heart attack, sudden death and loss of limb or function of a limb stemming from the stenosis. The reconstruction of blood vessels, arteries and veins may also be needed to treat individuals suffering from stenosis and restenosis. Coronary bypass can also be utilized to revascularize the heart and restore normal blood flow. In other cases, balloon angioplasty may be conducted to increase the orifice size of affected areas. Overall, these treatments address the problems associated with stenosis, but they also create a high rate of restenosis that can result in recurrence of cardiac symptoms and mortality. Moreover, these treatments are not preventative in nature, and therefore generally are not utilized until the patient or individual has already developed stenosis.

One type of stenosis and restenosis is atherosclerosis. Atherosclerosis affects medium and large arteries and is characterized by a patchy, intramural thickening that encroaches on the arterial lumen and, in most severe form, causes obstruction. The atherosclerotic plaque consists of an accumulation of intracellular and extracellular lipids, smooth muscle cells and connective tissue. The earliest lesion of atherosclerosis is the fatty streak that evolves into a fibrous plaque coating the artery. Atherosclerotic vessels have reduced systolic expansion and abnormal wave propagation. Treatment of atherosclerosis is usually directed at its complications, for example, arrhythmia, heart failure, kidney failure, stroke, and peripheral arterial occlusion.

New and improved methods and devices are being sought for treatment and prevention of vascular diseases such as stenosis, restenosis and atherosclerosis.

SUMMARY OF THE INVENTION

The present invention provides methods and devices for treating vascular diseases such as stenosis, restenosis and atherosclerosis.

More particularly, the present invention provides a method of treating or preventing restenosis in a living organism. The method comprises applying an effective amount of a composition comprising a sex hormone, anti-hormone, sex-hormone agonist, steroid-hormone inhibitor/antagonist (partial or full), selective estrogen receptor modulator (SERM), or a combination thereof, to a stent. The stent is inserted into an area of a living organism affected by restenosis. At least a portion of the sex hormone, anti-hormone, sex-hormone agonist, steroid-hormone inhibitor/antagonist (partial or full), selective estrogen receptor modulator (SERM), or combination thereof, is allowed to gradually release from the stent into the area of the living organism affected by the restenosis, thereby treating and preventing restenosis.

The invention also provides a local-delivery device for treating and preventing restenosis in a living organism. The device comprises a stent coated with a platform, natural carrier or pharmaceutical agent and an effective dose of a composition comprising estrogen, estradiol or a derivative thereof or combination of estrogen with other antiproliferative compound. Phosphoryicholine is one example of a pharmaceutical agent.

The platform, natural carrier or pharmaceutical agent at least partially encompasses the composition, thereby allowing for gradual release of the composition therefrom when the stent is inserted into an area of a living organism affected by restenosis.

The invention also provides another method of treating or preventing restenosis in a living organism. The method comprises applying an effective dose of a composition including estrogen, estradiol or a derivative thereof to a stent. The stent is inserted into an area of a living organism affected by restenosis in order to treat or prevent the same. At least a portion of the stent directly contacts the affected area.

BRIEF DESCRIPTION OF THE DRAWINGS

FIG. 1 is a perspective view of a stent embodying the invention.

FIG. 2 is a cross-sectional view taken along line 2—2 in FIG. 1.

FIG. 3 is a perspective view of a balloon-injection catheter embodying the invention.

FIG. 4 is cross-sectional view taken along line 4—4 of FIG. 3.

FIG. 5 is a cross-sectional view taken along line 4—4 in FIG. 5, wherein the catheter is inserted into an affected area of a living organism.

FIG. 7 is a table illustrating photomicrographs of histological section 30 days after delivery of a) control stent b) low dose 17B-estradiol stent, and c) high dose 17B-estradiol stent illustrating intimal proliferation.

FIG. 8 is a table illustrating dosage data for studies performed in Example 2.

FIG. 9 is a table showing averages and standard deviations for the dosage per stent and dosage per unit area.

FIG. 10 shows total dosage per stent for the various stent designs, which was estimated by multiplying the average dosage per unit area by the stent surface areas.

Figure 6:
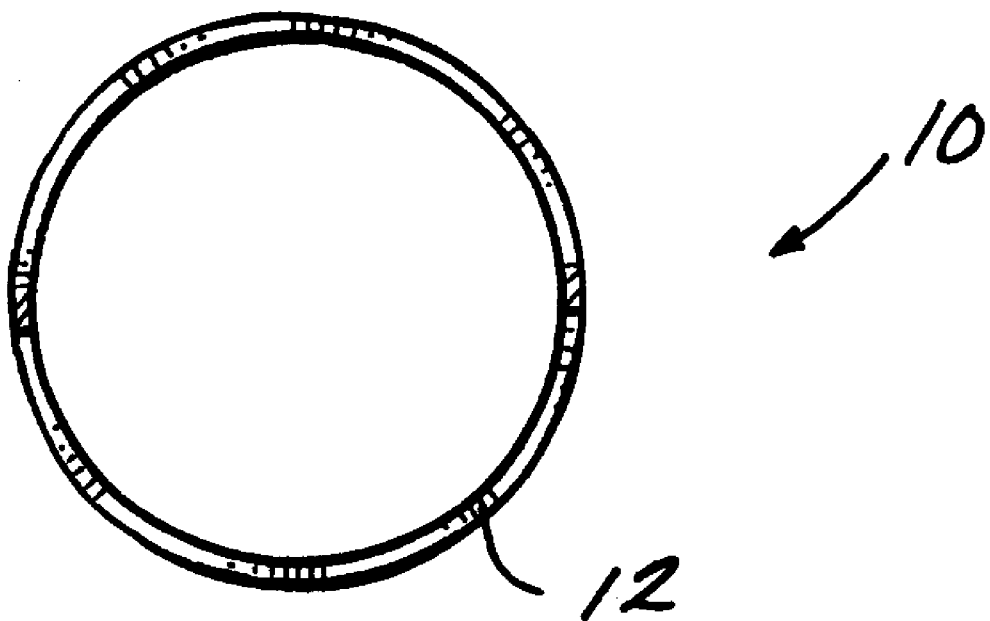
FIG. 6 is a cross-sectional view taken along line 6—6 of FIG. 1.

Other features and advantages of the invention will become apparent to those skilled in the art upon review of the following detailed description and claims. Before embodiments of the invention are explained in detail, it is to be understood that the invention is not limited in its application to the details of the composition and concentration of components set forth in the following description. The invention is capable of other embodiments and of being practiced or being carried out in various ways. Also, it is understood that the phraseology and terminology used herein is for the purpose of description and should not be regarded as limiting.

DESCRIPTION OF THE INVENTION

The present invention provides apparatuses and methods for delivering a composition to a localized area of a living organism. More particularly, the invention provides apparatuses and methods for locally delivering a sex hormone (e.g. estrogen), an anti-hormone, a sex-hormone agonist, a steroid-hormone inhibitor/antagonist (partial or full) or a selective estrogen receptor modulator (SERM), or a combination thereof, to a portion of a living organism inflicted by or susceptible to a vascular disease such as stenosis or restenosis.

Recent research has uncovered that different sex hormones may have different effects on vascular functions. For example, gender differences in cardiovascular disease have largely been attributed to the protective effects of estrogen in women; premenopausal women have a lower incidence of Coronary Heart Disease. In particular, estrogen has well-known beneficial effects on lipid profile. More importantly, estrogen may directly affect vascular reactivity, which is an important component of atherosclerosis. Recent epidemiological studies suggest that hormone replacement therapy (HRT) may reduce the risk of coronary-artery disease in post-menopausal women. More particularly, many epidemiological studies suggest that estrogen replacement therapy (ERT) may be cardioprotective in postmenopausal women. The beneficial effects of these hormone therapies may also be applicable to males. Unfortunately the systemic use of estrogen has limitations due to the possible hyperplastic effects of estrogen on the uterus and breast in women, and the feminizing effects in males.

The mechanisms for these beneficial effects are probably multifactorial. Estrogen is known to favorably alter the atherogenic lipid profile and may also have a direct action on blood vessel walls. Estrogen can have both rapid and long-term effects on the vasculature including the local production of coagulation and fibrinolytic factors, antioxidants and the production of other vasoactive molecules, such as nitric oxide and prostaglandins, all of which are known to influence the development of vascular disease.

Experimental work suggests that estrogen can also act on the endothelium and smooth muscle cells either directly or via estrogen receptors in both men and women. This appears to have an inhibitory effect on many steps in the atherosclerotic process. With respect to the interventional cardiology, estrogen appears to inhibit the response to balloon injury to the vascular wall. Estrogen can repair and accelerate endothelial cell growth in-vitro and in-vivo. Early restoration of endothelial cell integrity may contribute to the attenuation of the response to injury by increasing the availability of nitric oxide. This in turn can directly inhibit the proliferation of smooth muscle cells. In experimental studies, estrogen has been shown to inhibit the proliferation and migration of smooth muscle cells in response to balloon injury. Estrogen has also proved to inhibit adventitial fibroblast migration, which may in turn have an effect on negative remodeling.

Effective Compositions

Sex hormones and sex-hormone agonists may be helpful in preventing and treating certain vascular diseases. Examples of suitable sex hormones include, but are in no way limited to, estrogens, progesterones, testosterones, dehydroepiandrostrones (DHEAs) and dehydroepiandrosteronesulfates (DHEAs) and derivatives thereof. Of these compounds, estrogen has proven to be the most effective in preventing and treating vascular diseases. Naturally occurring/plant estrogens or phytoestrogens including isoflavones such as genistein, daidzein and resveratrol are also useful in the treatment of vascular disease. Suitable sex-hormone agonists include, but are in no way limited to, estradiol, estrone, ethinyl estradiol, conjugated equine estrogens and derivatives thereof In addition, anti-hormones and steroid-hormone inhibitors/antagonist (partial or full) may be effective in preventing vascular diseases. Anti-hormones inhibit or prevent the usual effects of certain other hormones, thereby increasing the relative effectiveness of hormones that are not being inhibited or prevented by these anti-hormones. Anti-hormones effective in preventing vascular diseases include, but are not limited to, anti-estrogens (e.g. Faslodex), anti-androgens (e.g. cyproterone acetate) and anti-testosterone (e.g. anti-testosterone wild-type Fab fragment and mutant Fab fragments). Examples of steroid-hormone inhibitors/antagonist (partial or full) include, but are not limited to, aminogluthemide, anastrazole and letrozole.

Selective estrogen receptor modulators (SERMS), including but not limited to raloxifene, tamoxifen and idoxifene, may also be effective in treating or preventing vascular diseases such as stenosis and restenosis.

These compounds are generally found in a powdered form. In order to apply the compound to a local-delivery device or to locally inject the compound into an affected area, the powder is generally mixed with a solution of saline or ethanol. This facilitates coating the local-delivery devices or injecting the composition as described below. The composition can also be mixed into another solution, gel or substance to control the rate of release from the stent and into the tissue.

Local-Delivery Systems

Local delivery of the above-listed compositions in the exact area of disease or potential disease avoids the negative systemic effects these compounds can produce when administered generally. For example, oral use of conjugated equine estrogen in combination with a progestin may have effects on the coagulation pathways that attenuate the benefits that may potentially occur to a vascular wall. In addition, hyperplastic effects of estrogen on the uterus and breast tissue may exist when estrogen is administered systemically. Moreover, general administration may result in potential feminizing effects in males.

The local delivery of estrogen and the other compositions described above to atherosclerotic plaque is a promising alternative to the systemic use of this hormone. The basic anti-atherogenic properties of these compositions and their potential to inhibit neointimal proliferation while simultaneously attenuating endothelial repair make them ideal for local administration in the coronary artery to inhibit restenosis. Localized delivery of other compositions comprising sex hormones, anti-hormones, sex-hormone agonists, steroid-hormone inhibitors/antagonist (partial or full) or selective estrogen receptor modulators (SERMS), or combinations thereof, to the vasculature may prevent and treat vascular diseases such as stenosis, restenosis and atherosclerosis.

The local-delivery systems generally comprise a local-delivery device and at least one of the effective compositions described above. The compositions can be delivered locally to tissue, tubular organs, blood vessels, the coronary or peripheral of organs as well as to muscles (myocardium, skeletal or smooth muscles). The compositions can also be injected directly into the vessel, vessel wall or muscle.

Examples of local-delivery devices include, but are not limited to, stents and catheters. In one embodiment of the invention, the local-delivery system is a stent that delivers the above-described compositions to the localized portion of the body of a living organism. FIG. 1 illustrates a stent 10, which is a hollow member that lies within the lumen of a tubular structure and provides support and assures patency of an intact but contracted lumen. Stents may be made from stainless steel or any other suitable material. Effective compositions as described above coat or are applied to the stent. FIG. 2 shows a portion of the stent 10 coated with a composition 12 in cross-section. Because the stent remains in the artery after the angioplasty procedure is performed, it enables the composition 12 to slowly diffuse from the outside of its surface 10 into the adjacent atherosclerotic plaque to which it can affect. The rate of this diffusion varies according to the molecular weight of the compound being administered. Also, the structure of the stent and the type of coating applied thereto also affect the rate of diffusion.

In another embodiment, an effective composition is applied to an injection catheter, and more particularly to a balloon-injection catheter 14. As shown in FIGS. 3 and 4, a balloon-injection catheter 14 is similar to a balloon angioplasty, except for the added feature of a chamber 16 including injection ports 18 for injecting the compositions described above. FIG. 5 illustrates a balloon-injection catheter 14 in cross-section after being injected into an affected area 20 of a living organism. The hormone can be injected directly into the plaque, vessel wall or tissue 22 via these injection ports 18. If an injection catheter injects the compound into the plaque 22, the composition releases immediately after injection. Accordingly, there is no residual release of the composition once the injection catheter is removed.

Angiographic, angioplasty, delivery and infusion catheters may also be used to deliver these compounds to affected areas. Using these devices, the above-described compositions can be locally delivered to a variety of body structures including grafts, saphenos vein grafts, arterial grafts, synthetic grafts, implants, prostheses or endoprostheses, homo or zeno grafts, cardiac muscle, skeletal or smooth muscle body structure.

Applying the Effective Compositions to the Local-Delivery Devices

Preferably, about 10 µg to about 3000 µg of effective composition can be applied to each stent or delivery device. More preferably, about 25 µg to about 2000 µg of effective composition can be applied to each stent or delivery device, and most preferably about 50 µg to about 1000 µg of effective composition can be applied to each stent or delivery device. In no way should these dosages be construed as limiting, as they are only preferred ranges. Effective dosages may widely vary; any dosage that restores circulation through a stenosed or restenosed blood vessel and/or alleviates the narrowing of the affected area is acceptable for use in the invention. As a result, dosages well in excess of the preferred ranges can be acceptable. The manner by which the effective compounds are bonded to the stent can also provide either slow or fast release of the effective compounds. Slow release of the effective compound can take up to ten years. Most preferably, release any period of time which allows for the effective compound to release from the stent or delivery device such that circulation is restored through the blood vessel and/or the narrowing of the affected area is alleviated is acceptable. Application of these effective compositions to a stent or other local-delivery device can be achieved in a number of different ways.

First, the compound can be mechanically or electromechanically bonded to the delivery device, e.g. by a covalent bonding process. When using such a physical application the compounds are directly embedded into a metal or other suitable substance from which the local-delivery system is comprised.

Second, the effective composition can also be applied using a chemical coating/bonding process, whereby layers of a suitable pharmaceutical agent, vehicle, or carrier entrap the compound. In this manner, a biological or pharmacological coating already present on the local-delivery device acts as a platform for coating the compounds described above. Examples of platforms include, but are not limited to, silicon carbide, carbon, diamond or diamond-like coating, e.g. polytetrafluoroethylene, hylauronic acid or polyactone. Other suitable synthetic pharmaceutical agents include, but are not limited to, phosphorylcholine, polyurethane, segmented polyurethane, poly-L-lactic acid, cellulose ester, polyethylene glycol as well as polyphosphate esters. Naturally occurring vehicles or carriers include collagens, laminens, heparins, fibrins, and other naturally occurring substances that absorb to cellulose. Using a chemical coating of the stent or other device is particularly advantageous in that it allows the compound or sex hormone to slowly release from the carrier, vehicle, or agent. This extends the time that the affected portion of the body sustains the efficacious effects of the compounds. The manner in which these carriers or vehicles interact with the device material as well as the inherent structure of these carriers and vehicles provide a diffusion barrier, thereby controlling the release of the entrapped compounds or sex hormones. In other words, the manner by which the effective compounds are chemically bonded to the stent or delivery device can control slow or fast delivery of the compound.

Estrogen and the other effective compositions described above can also be coated onto or delivered with other drugs or compounds in order to administer synergistic treatment. Examples of other suitable drugs and compounds include antibodies, oligonucleotides (e.g. antisense oligonucleotides), antiproliferatives, anticancer or antimicrotubular agents (e.g. rapamycin, paclitaxel), antiproliferative agents, growth factors, genes, antisense or antithrombotic agents or any other chemical or biological compound that will act synergistically to increase the effectiveness of the primary hormone or compound. For example, stent coatings can absorb and release these materials, thus providing an inert depot for controlled drug administration. Loading of the drug can occur for example via diffusion of the drug solution into the coating by hydration/swelling of the polymer matrix.

EXAMPLE 1

In one preferred example, powdered or liquid estrogen is mixed with a carrier such as ethanol to form a solution or gel. The estrogen gel is then applied to a stainless steel stent using chemical coating methods that are well-known in the art. Subsequently, the coated stent is inserted into an arterial lumen of a human being suffering from atherosclerosis. In other words, the coated stent is inserted into an artery plagued by patchy, intramural plaque. The estrogen in the coating slowly diffuses into and penetrates the plaque, thereby providing treatment for this vascular disease.

EXAMPLE 2

In another example, low and high dose 17B-estradiol eluting stents were compared with control stents in a randomized fashion in 18 porcine coronary arteries. Each artery of six pigs were randomly stented with either a control, low-dose or high-dose 17-estradiol eluting stent. All animals were sacrificed at 30 days for histomorphometric analysis.
Animal Preparation.

The experiment and animal care conformed to National Institutes of Health and American Heart Association guidelines for the care and use of animals and were approved by the Institutional Animal Care and Use Committee at the Washington Hospital Center. Six domestic juvenile swine weighing 35–45 kg were used. They were premedicated with acetylsalicyclic acid 350 mg for a day prior and 75 mg of clopidogrel for 3 days prior to the procedure and until sacrifice. The swines were sedated with a combination of ketamine (20 mg/kg) and xylazinc (2 mg/kg), by intramuscular injection. They were given pentobarbital (10–30 mg/kg IV), and were subsequently intubated and ventilated with oxygen (2 L/min) and isoflurane 1% (1.5 L/min). An 8F-introducer sheath was inserted into the right carotid artery by surgical cut down. Heparin (150 units/kg) was administered intra-arterially. Heart rate, blood pressure and electrocardiography were monitored throughout the procedure.
Protocol For Loading Of 17B-Estradiol Onto Stents Two-doses of 17B-estradiol powder (100 mg, dissolved in ethanol {5.0 ml}, Sigma, St. Louis, Mo.) were impregnated onto phosphorylcholine (PC) coated stainless steel stents (Biodiv Y sio™DD Stent {3.0 mm×18 mm}, Biocompatibles Ltd., Surrey, United Kingdom). The stents were immersed into the estradiol solution for 5 minutes and then allowed to dry at room temperature for another 5 minutes. For the high dose stent, a 10 $\mu$l aliquot of solution was pipette onto the stent and spread instantly and diffused into the stent. After being allowed to dry for 1 minute, this step was repeated and the stent was allowed to dry for 10 minutes prior to implantation. In vitro studies indicate that an estradiol dose of 67 $\mu$g (range: 51–88 $\mu$g) for the low dose stent and 240 $\mu$g (range: 229–254 $\mu$g) for the high dose can be loaded onto a 3.0×18 mm stent.
Stent Deployment Coronary angiography was performed after intracoronary nitroglycerin (200 $\mu$g) administration and recorded on cine film (Phillips Cardiodiagnost; Shelton, CT). Using high-pressure dilatation (12–14 atm ×30 sec), a single stent of each type was deployed in all 3 coronaries of each animal in a randomized fashion so that the 3 different types of stents were deployed in a different artery for each pig. The operator was blinded to the stent type being deployed. The stent artery ratio was kept between 1:1.3 and 1:1.2. All animals tolerated the stenting procedure and survived until 30 days after which they were sacrificed and the hearts were perfusion-fixed.
Ouantitative Histomorphometric Anaysts The histopathologist was blinded to the stent types in each artery. Cross sections of the stented coronary arteries were stained with metachromatic stain (Stat Stain for Frozen Sections, Eng. Scientific, Inc., 82 Industrial Fast, Clifton, N.J., 07012), Area measurements were obtained by tracing the external elastic lamina (vessel area, VA, mm$^2$) stent line (stent strut area, mm$^2$) lumen perimeter (luminal area, LA, mm$^2$) and neointimal perimeter (intimal area, IA, mm$^2$). The vessel injury score was determined by the method described by Kornowski et al. The scoring of endothelialization is based on percent of intimal surface covered by endothelial cells. 1+ equals less than ¼ of the intimal surface is covered by endothelial cells, 2+ equals over ¼ and less than ¾ covered and 3+ equals greater than ¾ to complete coverage of the intimal surface.
Statistical Analysis Data (mean±standard deviation) were analyzed to determine differences between treatment groups using an ANOVA with a post-hoc Bonferroni analysis. Comparison of the mean values with a p-value of less than 0.05 was considered statistically significant.

There was a 40% reduction in intimal area in the high dose stents compared with control stents (2.54±1.0 mm$^2$ vs 4.13±1.1 mm$^2$, for high dose vs control respectively, P<0.05. see Table 1.). There was also a reduction in the IA/Injury score ratio in the high dose group compared with the control stents (1.32±0.40 mm$^2$ vs 1.96±0.32 mm$^2$, for high dose vs control respectively, P<0.01, see Table 1.). FIG. 7a) illustrates the histological appearance of the control stented segments at 30 days. FIG. 7b) illustrates the histological appearance of the low-dose stented segments at 30 days and FIG. 7c) illustrates the histological appearance of the high dose stented segments at 30 days. More than ¾ to complete coverage with endothelium was observed in all 3 groups (endothelialization score=3+). There was 3+ endothelialization score observed in all the stent groups.

This is the first study to show that 17B-estradiol eluting stents reduce intimal proliferation without effecting endothelial regeneration in the pig model of instent restenosis. Estrogen coated stents prevent and treat instent restenosis.

The basic anti-atherogenic properties of estrogen with the potential to inhibit neointimal proliferation whilst not effecting endothelial repair appears to make estrogen an ideal compound to be delivered on a stent. Previous research has shown that a single intracoronary infusion of estrogen can inhibit smooth muscle cell proliferation in the pig after angioplasty.

The pathophysiology of restenosis involves neointimal hyperplasia and negative vessel remodeling. Although the low dose 17B-estradiol stents only demonstrated a trend towards a reduction in intimal area, the high dose 17B-estradiol stents significantly inhibited the neo-intimal proliferative response by about 40% compared with control stents.

One of the major limitations of current therapies for restenosis such as brachytherapy is that of late stent thrombosis. A delay in re-endothelialization causing a persistent thrombogenic coronary surface is the most plausible explanation for this side effect. There was no evidence of inhibition of endothelial cell regeneration in the low or high dose stented arteries compared with control.

These 2 findings were observed with the use of a relatively low systemic dose of estrogen. Systemic doses usually range between 25–30 µg/kg, which is more than 2–3 the total dose of estrogen loaded onto the high dose stent. In fact, many clinical studies have acutely administered higher doses (systemically or intracoronary) in both male and females with no untoward effects. If hypothetically the entire, high dose (264 µg), were eluted from the stent into the systemic circulation as a single bolus, no side effects would be expected. The delivery of a relatively low dose of estrogen directly on a stent to inhibit restenosis without impeding endothelial regeneration represents a major theoretical advantage over radiation therapy and perhaps other locally delivered anti-proliferative drugs.

Consequently, this demonstrate that estrogen impregnated stents reduce the intimal proliferative response to stent implantation without impeding re-endothelialization. Since 17B-estradiol is an endogenous circulating hormone in both males and females, in this relatively low systemic dose, it may provide a simple, non-toxic therapy for treating de novo coronary lesions, small vessels and diffuse disease.

We claim:

1. A local-delivery device for treating and preventing restenosis in a living organism, the device comprising:

a stent coated with a platform, natural carrier of pharmaceutical agent; and an effective dose of a composition comprising estrogen, stradiol or a derivative thereof, wherein the platform, natural carrier of pharmaceutical agent at least partially encompasses the composition, thereby allowing for gradual release of the composition therefrom when the stent is inserted into an area of a living organism affected by restenosis.

2. The device of claim 1, wherein the pharmaceutical agent is phosphorylcholine.

3. The device of claim 2, wherein the effective dose of the composition is about 50 µg to about 1000 µg.

4. The device of claim 2, wherein the effective dose of the composition is about 50 µg to about 276 µg.

5. The device of claim 2, wherein the effective dose of the composition is about 2.4 µg to about 3.2 µg per 1 mm$^2$ of stent.

6. The device of claim 1, wherein the composition further comprises a sex hormone, anti-hormone, sex-hormone agonist, steroid-hormone inhibitor/antagonist (partial or full), selective estrogen receptor modulator (SERM) or combination thereof.

7. The device of claim 1, wherein the composition further comprises an antibody, oligonucleotide, antiproliferative, anticancer agent, growth factor, gene, antithrombotic agent or combination thereof.

* * * * *

UNITED STATES PATENT AND TRADEMARK OFFICE
CERTIFICATE OF CORRECTION

PATENT NO. : 6,471,979 B2
DATED : October 29, 2002
INVENTOR(S) : Gishel New et al.

It is certified that error appears in the above-identified patent and that said Letters Patent is hereby corrected as shown below:

Column 9,
Line 23, delete "of" and insert in its place -- or --.
Line 26, delete "stradiol" and insert in its place -- estradiol --.

Column 10,
Line 1, delete "of" and insert in its place -- or --.

Signed and Sealed this

First Day of April, 2003

JAMES E. ROGAN
*Director of the United States Patent and Trademark Office*